US00PP23270P3

(12) United States Plant Patent
Johnson, Jr. et al.

(10) Patent No.: US PP23,270 P3
(45) Date of Patent: Dec. 25, 2012

(54) BLACKBERRY PLANT NAMED 'HJ-6'

(50) Latin Name: *Rubus ursinus*
Varietal Denomination: HJ-6

(75) Inventors: Harold A. Johnson, Jr., Aromas, CA (US); Judith E. Johnson, Aromas, CA (US)

(73) Assignee: Plant Sciences, Inc., Watsonville, CA (US)

( * ) Notice: Subject to any disclaimer, the term of this patent is extended or adjusted under 35 U.S.C. 154(b) by 17 days.

(21) Appl. No.: 13/064,117

(22) Filed: Mar. 7, 2011

(65) Prior Publication Data

US 2011/0219496 P1 Sep. 8, 2011

Related U.S. Application Data

(60) Provisional application No. 61/311,466, filed on Mar. 8, 2010.

(51) Int. Cl.
*A01H 5/00* (2006.01)

(52) U.S. Cl. ..... Plt./203; Plt./204

(58) Field of Classification Search ..... Plt./203, Plt./204
See application file for complete search history.

(56) References Cited

U.S. PATENT DOCUMENTS

2011/0219496 P1 * 9/2011 Johnson et al. ..... Plt./203
* cited by examiner

*Primary Examiner* — Susan McCormick Ewoldt
(74) *Attorney, Agent, or Firm* — Foley & Lardner LLP

(57) ABSTRACT

This invention relates to a new and distinct variety of blackberry plant named 'HJ-6'. The new variety resulted from seed produced by a hand-pollinated cross of two non-patented varieties: "Obsidian" as the female, and "Eaton" as the male. The new, trailing cultivar can be distinguished by its consistent, large fruit size and appearance during the late spring and summer period for the fresh market. The fruit of this cultivar is produced on dark red, strong, thorny canes. When plants are grown and pruned correctly, yield in central California, USA can be up to 9,000 crates/acres, and the fruit ships well.

2 Drawing Sheets

CROSS-REFERENCE TO RELATED APPLICATIONS

Figure 1:
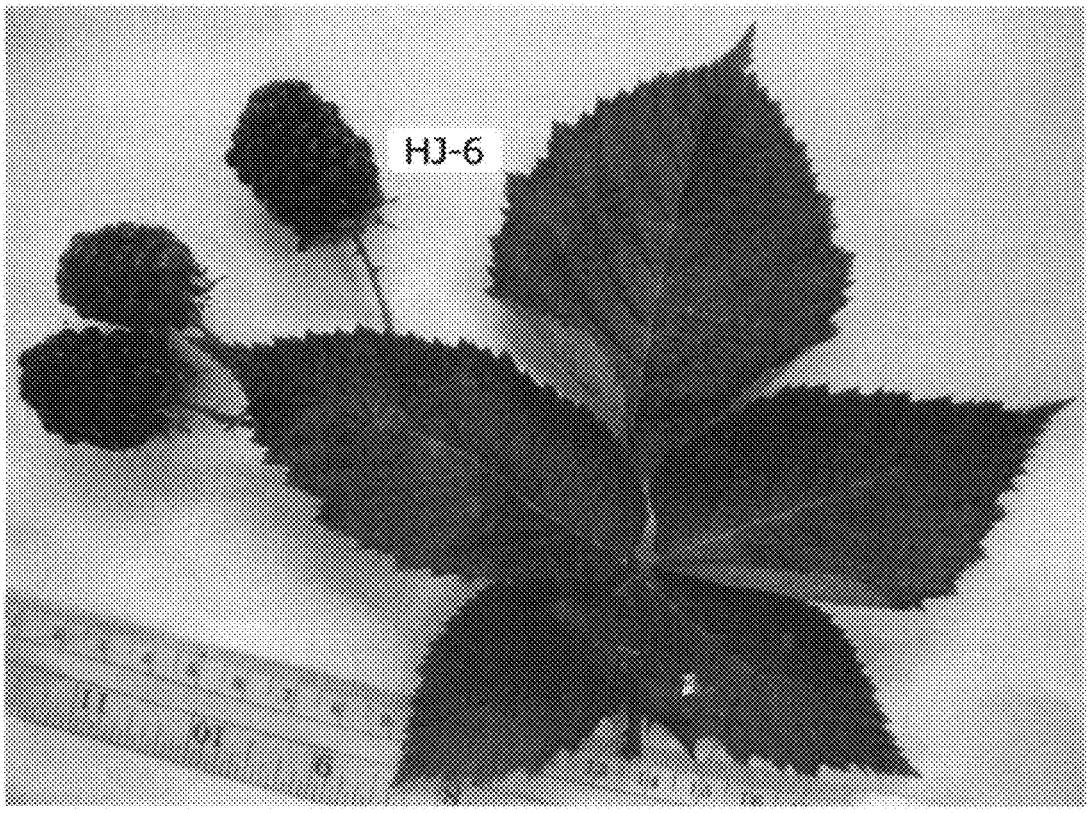

This application claims priority from U.S. Provisional Application No. 61/311,466 filed Mar. 8, 2010, incorporated herein by reference in its entirety.

BACKGROUND OF THE INVENTION

The present invention relates to a new and distinct trailing blackberry variety designated as 'HJ-6'. This new variety is a result of a controlled cross made by the inventors, Harold A. Johnson Jr. and Judith E. Johnson, in 2005 between the blackberry variety designated 'Obsidian' (female) and the blackberry variety designated 'Eaton' (male), both parental varieties unpatented. The variety 'HJ-6' is botanically known as *Rubus ursinus*.

The seedling resulting from the aforementioned cross was selected from a controlled breeding plot near Watsonville, Santa Cruz County, Calif. in 2007 by the inventors. After its selection, the new variety was further asexually propagated beginning in October of 2007 in Watsonville, Santa Cruz County, Calif. by tissue culture. The new variety was then tested in fruiting fields in Santa Cruz County, Calif. This propagation has demonstrated that the combination of traits disclosed herein as characterizing the new variety are fixed and remain true to type through successive generations of asexual reproduction.

SUMMARY OF THE INVENTION

'HJ-6' is primarily adapted to the climate and growing conditions of the Santa Cruz and Monterey Counties in Calif., and is being tested in Ventura County, Calif., and in Europe. 'HJ-6' has reacted favorably to the coastal climates of northern coastal California, but for maximum fruit production, 'HJ-6' requires consistent soil moisture and adequate nutrition. 'HJ-6' reacts favorably to an environment created by plastic tunnels.

The following traits have been observed and are determined to be unique characteristics of 'HJ-6', which in combination distinguish this blackberry plant as a new and distinct variety.

1. consistent production of large in size and good quality fruit, regardless of the time of year and the age of the plant;
2. large fruit size responds favorably to careful packing when shipped in 6 oz. clamshell baskets;
3. thorny and trailing plant structure; and
4. late spring fruit production, starting in June, with peak production in late June, and continued, limited production through July and August, when grown in Santa Cruz County, Calif.

When the new blackberry variety 'HJ-6' is compared to the female parental variety 'Obsidian', the following trait differences have been observed:

1. the peak fruit production of 'HJ-6' occurs later than 'Obsidian', but earlier than most erect types;
2. in holding testing after picking, the average flavor rating was the same, but HJ-6 rated higher in appearance than Obsidian after various days in cold storage;
3. HJ-6 has produced more commercial quality fruit in crates per acre than 'Obsidian', and a smaller percentage of non-commercial quality fruit per acre;

4. the average soluble solids concentration of Obsidian is 10.8, and HJ-6 is 9.3; and
5. the average seed size of HJ-6 is is 3.54 mm in length and 1.93 mm in width, and Obsidian is 3.52 mm in length and 1.93 mm in width.

When the new blackberry variety 'HJ-6' is compared to the male parental variety 'Eaton', the following trait differences have been observed:

1. the fruit size of 'HJ-6' is consistently larger than the fruit of 'Eaton';
2. the fruit shape of 'HJ-6' is medium ovate while the fruit shape of 'Eaton' is long and conic;
3. 'HJ-6' has determinate inflorescence which limits the number of peduncles as well as the length and number of each pedicel per plant leading to a limited number of berries which are larger in size, whereas 'Eaton' has indeterminate inflorescence which produces a larger number of smaller berries per plant;
4. 'HJ-6' has an abundant supply of pollen which leads to a minimum number of malformed fruit, whereas 'Eaton' lacks consistently good pollen at the end of its indeterminate infloresences and thus often produces poorly-shaped, small fruit;
5. 'HJ-6' has larger leaves than 'Eaton'; and
6. 'HJ-6' has stronger overall vegetative strength than 'Eaton'.

When the new blackberry variety 'HJ-6' is compared to the similar variety 'HJ-7' (U.S. Ser. No. 13/385,249), the following trait differences have been observed:

1. the fruit production of 'HJ-6' occurs later in the season than 'HJ-7';
2. the overall (total season) production of 'HJ-6' is greater than that of 'HJ-7';
3. the average berry size of 'HJ-6' (8-10 g) is larger than the average berry size of 'HJ-7' (6-7 g);
4. the leaf color of 'HJ-6' is lighter in early June (7.5 GY4-4) than the leaf color of 'HJ-7' at the same point in the season (7.5 GY3-2); and
5. 'HJ-6' is considered superior to 'HJ-7' in side-by-side flavor test results.

BRIEF DESCRIPTIONS OF THE PHOTOGRAPHS

The accompanying color photographs illustrate the overall appearance of typical specimens of the new blackberry variety, 'HJ-6' as true as reasonably possible with color reproductions of this type. Plants shown in the photographs are two years old.

FIG. 1, taken in October 2009, illustrates the typical large fruit produced by 'HJ-6' that is long-conical to oblong in shape, contains large druplets, and has thorns on the pedicel. FIG. 1 further illustrates the typical foliage produced by HJ-6; that comprises mostly 5 leaflets, each leaflet being ovate to oblique in shape, with an acuminate to acute apex, bi-serrate serrations, and palmate venation. The leaf petiole, as well as, the fruit peduncle, as further illustrated in FIG. 1, has a red surface.

Figure 2:
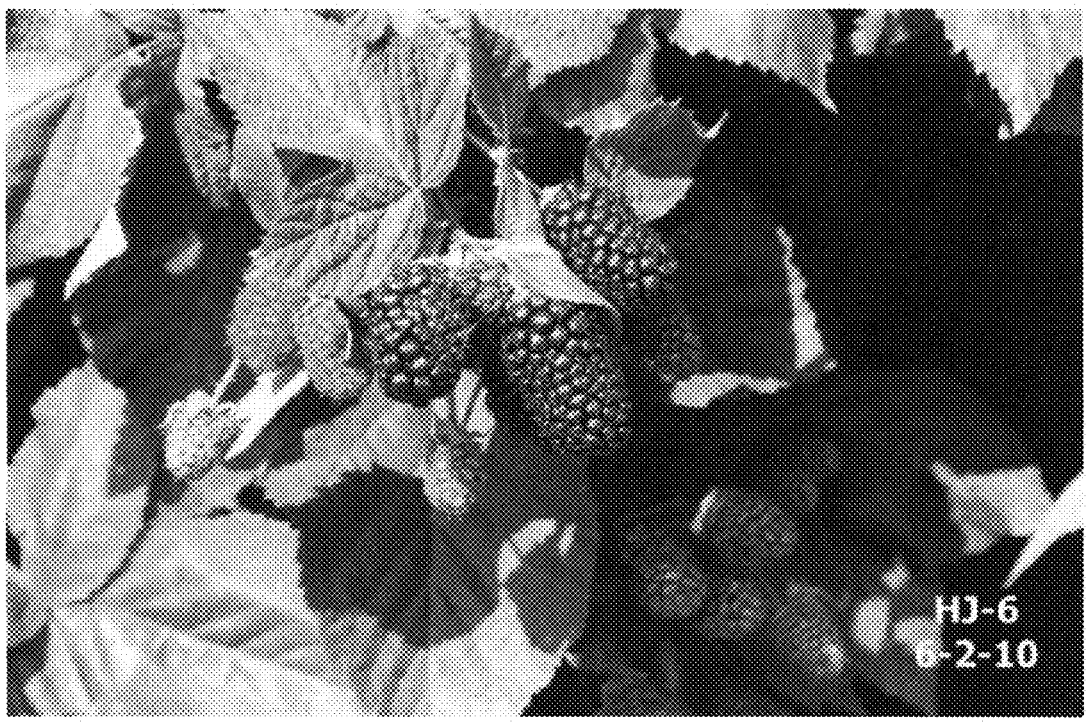

FIG. 2, taken in June 2010, illustrates the fruit size and short pedicels of a typical inflorescence that is held mainly near or on the exterior of a plant in early June. The fruit is presented mostly accessible to pickers. The drupelets are typical in size and appearance. The leaflets and their serrations are typical.

DETAILED BOTANICAL DESCRIPTION

The following description of 'HJ-6' unless otherwise noted, is based on observations taken during the 2008 and 2009 growing seasons in Santa Cruz County, Calif. The plants observed were two years old. The phenotypical descriptions and color designations stated for the new variety may vary, depending upon variations in environmental factors, including weather (temperature, humidity and light intensity), day length, soil type, location and cultural conditions. 'HJ-6' has not been observed under all possible environmental conditions.

Table 1 provides a botanical comparison of 'HJ-6' to the following two (2) unpatented, commercially grown varieties in Santa Cruz County, Calif.: (1) 'Obsidian', a trailing, semi-erect, thorny and early ripening variety (female parental variety), and (2) 'Chester Thornless', an erect, thornless, and late ripening variety.

TABLE 1

Botanical Comparison with Comparison Varieties

| CHARACTERISTIC | New Variety 'HJ-6' | Comparison Variety 1 OBSIDIAN (unpatented) | Comparison Variety 2 'CHESTER THORNLESS' (unpatented) |
|---|---|---|---|
| Plant Form | | | |
| Growth Habit | Trailing, semi-upright | Trailing, semi-upright | Semi-erect |
| Plant Height | 4 to 5 feet | 4 to 5 feet | 5 to 6 feet |
| Suckering | Abundant | Abundant | Abundant |
| Branching | Indeterminate | Indeterminate | Indeterminate |
| Cane Texture | Thorny | Thorny | Smooth |
| Hardiness | Very Hardy | Very Hardy | Very Hardy |
| Canes | | | |
| Diameter | Large—1.8 cm | Medium—1.2 cm | Large—1.2-2.0 cm |
| Floricane | Same Diameter | Same Diameter | Same Diameter |
| Immature Primocane | Round to Angular | Round to Angular | Angular |
| Color | | | |
| Prickles | Red to Green | Red to Green | None |
| Mature Canes | All red 2.5 R 2/2 | Upper side red 2.5 R 2/6 | Upper side red 2.5 R 2/7 |
| Foliage | Robust, large leaves | Robust, medium leaves | Robust, late-emergence |
| Predominate Number of Leaflets | Mostly 5, some 3 | Mostly 3, 4 and 5 | Mostly 5, some 3 |
| Leaf Type | Mainly palmate | Odd palmate to intermediate | Mainly palmate |
| Leaf Color | | | |
| Upper Surface | 5 GY 3/4 | 5 GY 3/4 | 10 GY 2/4 |
| Lower Surface | 7.5 GY 5/6 | 7.5 GY 5/6 | 7.5 GY 6/6 |
| Central Leaflet Shape | Ovate with acuminate apex | Ovate with acute to acuminate apex | Ovate with acuminate apex |
| Leaflet Relief Between Veins | Medium | Strong | Strong |
| Spine Attitude | Outward, some down | Mainly outward | No spine |
| Serrations of Leaflets | Shallow | Shallow | Shallow |
| Leaf Incision of Margin | Bi-serrate | Bi-serrate | Bi-serrate |
| Pubescence | Infrequent, no glandular hairs | Abundant, no glandular hairs | Infrequent, no glandular hairs |
| Petioles | | | |
| Color | Top—2.5 R 2/2 Bottom—5 GY 2/2 | Predom. 5 GY 2/2 | Predom. 5 GY 2/2 |
| Texture | Smooth, small thorns | Predom. smooth | Smooth |

TABLE 1-continued

Botanical Comparison with Comparison Varieties

| CHARACTER-ISTIC | New Variety 'HJ-6' | Comparison Variety 1 OBSIDIAN (unpatented) | Comparison Variety 2 'CHESTER THORNLESS' (unpatented) |
|---|---|---|---|
| Length | 4-6 cm | 3-5 cm | 2-3 cm |
| Width | 2-2.5 mm | 1.5-2 mm | 1.5-2 mm |
| Flowers | | | |
| Blooming Period | Mid-March to April | Early March to April | June |
| Pedicels | Short—3-6 cm | Medium—3-6 cm | Short pedicels on raceme peduncle |
| Petals | | | |
| Number | 5 to 6 | 5 | 5 |
| Shape | Irregular elliptical | Irregular elliptical | Irregular elliptical |
| Color | White; N9 25/84 2% R | White; N9 25/84 2% R | Pink, 2.5 RP 5/10 |
| Pollen | Strong | Strong | Strong |
| Sepals | | | |
| Number | 5 | 5 | 5 |
| Length | 5-10 mm; some with leaf extensions | 4-8 mm; some with leaf extensions | 4-6 mm; no leaf extensions |
| Fruit | | | |
| Productivity | Medium-high; long picking season | High | Medium |
| Time of Fruiting | Late spring to summer, June-July | Late May to July | August to September |
| Size | Very large; avg. 8 gm | Medium-large; avg. 6 gm | Medium-large; avg. 6-8 gm |

TABLE 1-continued

Botanical Comparison with Comparison Varieties

| CHARACTER-ISTIC | New Variety 'HJ-6' | Comparison Variety 1 OBSIDIAN (unpatented) | Comparison Variety 2 'CHESTER THORNLESS' (unpatented) |
|---|---|---|---|
| Shape | Oblong to conic | Elliptical, some circular | Oblong to conic |
| Color | | | |
| Immature | Green to red | Green to red | Green to red |
| Mature | N 1.75/2.5% R | N 1.75/2.5% R | N 1.75/2.5% R |
| Glossiness | Medium to Full | Medium to Full | Very glossy |
| Weight | 6 to 12 gm | 6 to 8 gm | 6 to 10 gm |
| Length | 30 to 35 mm | 25 to 30 nun | 25 to 30 mm |
| Diameter | 20 to 25 mm | 20 to 25 nun | 20 to 30 mm |
| Drupelets | | | |
| Size | 3 to 4 mm | 2.5 to 3 mm | 3 to 4.5 mm |
| Seed | | | |
| Length | 3.54 mm | 3.52 mm | 3.35 mm |
| Width | 1.93 mm | 1.92 mm | 1.96 mm |
| Soluble Solids | 9.2% | 10.8% | |
| pH | | | |
| Yield | 9343 crates/acre avg. | 6824 crates/acre avg. | |
| Disease/Pest Resistance | Red mite susceptible | Red mite susceptible | Red mite susceptible |
| Uses | Fresh market | Fresh market; processing | Fresh market |

When color is identified, the Munsell Book of Color (March 1976) is used.
Yield—crates/acre (crate = 4.5 lb)

What is claimed is:

1. A new and distinct plant of *Rubus Ursinus,* as herein described and illustrated by the characteristics set forth above.

* * * * *